United States Patent [19]
Reuser et al.

[11] Patent Number: 6,118,045
[45] Date of Patent: Sep. 12, 2000

[54] LYSOSOMAL PROTEINS PRODUCED IN THE MILK OF TRANSGENIC ANIMALS

[75] Inventors: Arnold J. J. Reuser, Rotterdam; Ans T. Van der Ploeg, Poortugaal; Frank R. Pieper, Utrecht; Martin Ph. Verbeet, Amsterdam, all of Netherlands

[73] Assignees: Pharming B.V.; The Universiteit Leiden, both of Leiden; Academic Hospital; Eramus Universiteit, both of Rotterdam, all of Netherlands

[21] Appl. No.: 08/700,760

[22] Filed: Jul. 29, 1996

Related U.S. Application Data

[60] Provisional application No. 60/001,796, Aug. 2, 1995.
[51] Int. Cl.[7] .................... A01K 67/00; A61K 39/395; A61K 35/20; A61K 38/47
[52] U.S. Cl. ...................... 800/14; 800/7; 800/21; 119/DIG. 1; 424/157.1; 424/535; 424/94.61
[58] Field of Search .............. 119/DIG. 1; 800/2, 800/DIG. 1–4, 14, 7, 21; 435/172.3; 424/450, 157.1, 535, 94.61; 20/23.1; 530/350

[56] References Cited

U.S. PATENT DOCUMENTS

| | | | |
|---|---|---|---|
| 5,356,804 | 10/1994 | Desnick et al. | 435/208 |
| 5,565,362 | 10/1996 | Rosen | 435/320.1 |

FOREIGN PATENT DOCUMENTS

| | | | |
|---|---|---|---|
| WO 93/25567 | 12/1993 | WIPO | 800/2 |

OTHER PUBLICATIONS

Belen'kil et al. Purification and Properties of Acid Alpha–Glucosidase (gamma–Amylase) from Human Liver. Biochemistry, vol. 40, No. 5, pp. 793–798, 1976.
de Barsy et al. Enzyme Replacement in Pompe Disease: An Attempt with Purified Human Acid Alpha–Glucosidase. Birth Defects Original Article Series, vol. 9, No. 2, pp. 184–190, Mar. 1973.
Minamiura et al. Identity of alpha–Glucosidas of Human Kidney with Urine F–1 alpha–Glucosidase. J. Biochemistry, vol. 91, pp. 809–816, 1982.
Obara et al. Mutual relationship between milk components and lysosome enzymatic activity in abnormal milk. Japanese Journal of Veterinary Scienc, vol. 45, No. 2, pp. 203–208, 1983.
Oberkotter et al. N–acetyl–beta–hexosaminidase activity in human breast milk. International Journal of Biochemistry, vol. 14, No. 2, pp. 151–154, 1982.
Barnes et al. Homology of lysosomal enzymes and related prediction of posttranslational modification sites including phosphorylation of mannose and potential epitopic and substrate binding sites in the alpha and beta subunits of hexosaminisases, 1988.
Bresciani et al. Lysosomal acid phosphatase is not involved in the dephosphorylation of mannose 6–phosphate containing lysosomal proteins. Eur. J. of Cell Biol. vol. 58, No. 1, pp. 57–61, Jun. 1992.
Houdebine L. M. Production of pharmaceutical proteins from transgenic animals. J. of Biotech. vol. 34, pp. 269–287, 1994.
Agnes G. A. Bijvoet et al., "Expression of cDNA–Encoded Human Acid α–Glucosidase in milk of Transgenic Mice," *Biochimica and Biophysica Acta*, vol.1308, 1996, pp. 93–96 (XP000609555).
Henri Rochefort et al., "The Estrogen–Regulated 52K–Cathespin–D in Breast Cancer: From Biology to Clinical Applications," *Nuclear Medicine and Biology*, vol. 14, No. 4, 1987, pp. 377–384 (XP000609069).
A. T. Van der Ploeg et al., "Intravenous Administration of Phosphorylated Acid α–Glucosidase Leads to Uptake of Enzyme in Heart and Skeletal Muscle of Mice," *The Journal of Clinical Investigation*, vol. 87, No. 2, Feb. 1991, pp. 513–518 (XP000609448).
Lies H. Hoefsloot et al., "Expression and Routeing of Human Lysosomal α–Glucosidase in Transiently Transfected Mammalian Cells," *Biochemical Journal*, vol. 272, 1990, pp. 485–492 (XP000609457).
Gerard J. Platenburg et al., "Expression of Human Lactoferrin in Milk of Transgenic Mice," *Transgenic Research*, vol. 3, 1994, pp. 99–108, (XP002024692).

*Primary Examiner*—Deborah J. Clark
*Attorney, Agent, or Firm*—Townsend & Townsend & Crew

[57] ABSTRACT

The invention provides transgenic nonhuman mammals producing phosphorylated lysosomal proteins in their milk, and methods of generating the same. Phosphorylation occurs at the 6' position of a mannose side chain residue. Also provided are methods of purifying lysosomal proteins from milk, and incorporating the proteins into pharmaceutical compositions for use in enzyme replacement therapy.

20 Claims, 7 Drawing Sheets

LYSOSOMAL PROTEINS PRODUCED IN THE MILK OF TRANSGENIC ANIMALS

CROSS-REFERENCE TO RELATED APPLICATION

The present application is a continuation-in-part of U.S. Ser. No. 60/001,796, filed Aug. 2, 1995.

TECHNICAL FIELD

The present invention relates to the production of mannose 6-phosphate containing lysosomal proteins in the milk of transgenic mammals, and administration of the proteins to patients suffering from disease resulting from deficiencies in corresponding endogenous proteins.

BACKGROUND

Like other secretory proteins, lysosomal proteins are synthesized in the endoplasmic reticulum and transported to the Golgi apparatus. However, unlike most other secretory proteins, the lysosomal proteins are not destined for secretion into extracellular fluids but into an intracellular organelle. Within the Golgi, lysosomal proteins undergo special processing to equip them to reach their intracellular destination. Almost all lysosomal proteins undergo a variety of posttranslational modifications, including glycosylation and phosphorylation via the 6' position of a terminal mannose group. The phosphorylated mannose residues are recognized by specific receptors on the inner surface of the Trans Golgi Network. The lysosomal proteins bind via these receptors, and are thereby separated from other secretory proteins. Subsequently, small transport vesicles containing the receptor-bound proteins are pinched off from the Trans Golgi Network and are targeted to their intracellular destination. See generally Kornfeld, *Biochem. Soc. Trans.* 18, 367–374 (1990).

There are over thirty lysosomal diseases, each resulting from a deficiency of a particular lysosomal protein, usually as a result of genetic mutation. See, e.g., Cotran et al., *Robbins Pathologic Basis of Disease* (4th ed. 1989) (incorporated by reference in its entirety for all purposes). The deficiency in the lysosomal protein usually results in harmful accumulation of a metabolite. For example, in Hurler's, Hunter's, Morquio's, and Sanfilippo's syndromes, there is an accumulation of mucopolysaccharides; in Tay-Sachs, Gaucher, Krabbe, Niemann-Pick, and Fabry syndromes, there is an accumulation of sphingolipids; and in fucosidosis and mannosidosis, there is an accumulation of fucose-containing sphingolipids and glycoprotein fragments, and of mannose-containing oligosaccharides, respectively.

Glycogen storage disease type II (GSD II; Pompe disease; acid maltase deficiency) is caused by deficiency of the lysosomal enzyme acid α-glucosidase (acid maltase). Three clinical forms are distinguished: infantile, juvenile and adult. Infantile GSD II has its onset shortly after birth and presents with progressive muscular weakness and cardiac failure. This clinical variant is fatal within the first two years of life. Symptoms in adult and juvenile patients occur later in life, and only skeletal muscles are involved. The patients eventually die due to respiratory insufficiency. Patients may exceptionally survive for more than six decades. There is a good correlation between the severity of the disease and the residual acid α-glucosidase activity, the activity being 10–20% of normal in late onset and less than 2% in early onset forms of the disease (see Hirschhorn, *The Metabolic and Molecular Bases of Inherited Disease* (Scriver et al., eds., 7th ed., McGraw-Hill, 1995), pp. 2443–2464).

Since the discovery of lysosomal enzyme deficiencies as the primary cause of lysosomal storage diseases (see, e.g, Hers, *Biochem. J.* 86, 11–16 (1963)), attempts have been made to treat patients having lysosomal storage diseases by (intravenous) administration of the missing enzyme, i.e., enzyme therapy. For lysosomal diseases other than Gaucher disease the evidence suggests that enzyme therapy is most effective when the enzyme being administered is phosphorylated at the 6' position of a mannose side chain group. For glycogenesis type II this has been tested by intravenously administering purified acid α-glucosidase in phosphorylated and unphosphorylated forms to mice and analyzing uptake in muscle tissue. The highest uptake was obtained when mannose 6-phosphate-containing enzyme was used (Van der Ploeg et al., *Pediat. Res.* 28, 344–347 (1990); *J. Clin. Invest.* 87, 513–518 (1991)). The greater accumulation of the phosphorylated form of the enzyme can be explained by uptake being mediated by a mannose-6-phosphate receptor present on the surface of muscle and other cells.

Some phosphorylated lysosomal enzymes can, in theory, be isolated from natural sources such as human urine and bovine testis. However, the production of sufficient quantities of enzyme for therapeutic administration is difficult. An alternative way to produce human acid α-glucosidase is to transfect the acid α-glucosidase gene into a stable eukaryotic cell line (e.g., CHO) as a cDNA or genomic construct operably linked to a suitable promoter.

Mammalian cellular expression systems are not entirely satisfactory for production of recombinant proteins because of the expense of propagation and maintenance of such cells. An alternative approach to production of recombinant proteins has been proposed by DeBoer et al., WO 91/08216, whereby recombinant proteins are produced in the milk of a transgenic animal. This approach avoids the expense of maintaining mammalian cell cultures and also simplifies purification of recombinant proteins.

Although the feasibility of expressing several recombinant proteins in the milk of transgenic animals has been demonstrated, it was unpredictable whether this technology could be extended to the expression of lysosomal proteins containing mannose 6-phosphate. Because typical secretory proteins like the milk proteins do not contain mannose groups phosphorylated at the 6' position, it was uncertain whether these cells possessed the necessary complement and activity of enzymes for phosphorylation of substantial amounts of an exogenous lysosomal protein. Further, if such cells did possess the necessary complement of enzymes, it would have appeared likely that phosphorylation would target the phosphorylated lysosomal protein via the mannose 6-phosphate receptor to an intracellular location rather than to an extracellular location. Substantial intracellular accumulation of a lysosomal protein might have been expected to have harmful or fatal consequences to the mammary gland function of the transgenic animal.

Notwithstanding the above uncertainties and difficulties, the invention provides inter alia healthy transgenic mammals secreting authentically phosphorylated lysosomal proteins in their milk.

SUMMARY OF THE INVENTION

In one aspect, the invention provides transgenic nonhuman mammals producing a lysosomal protein in their milk. The lysosomal protein is phosphorylated at the 6' position of a mannose side chain residue, The transgenic mammals have a transgene in their genome. The transgene comprises a mammary-gland specific promoter, a mammary-gland specific enhancer, a secretory DNA segment encoding a signal peptide functional in mammary secretory cells of the transgenic nonhuman mammal, and a recombinant DNA segment encoding a lysosomal protein, usually an enzyme. The recombinant DNA segment is operably linked to the secretory DNA segment to form a secretory-recombinant DNA segment. The secretory-recombinant DNA segment is in turn operably linked to the promoter and to the enhancer. The transgene, in an adult form of the nonhuman mammal or a female descendant of the nonhuman mammal, is capable of expressing the secretory-recombinant DNA segment in the mammary secretory cells to produce a form of the lysosomal protein that is processed and secreted by the mammary secretory cells into milk as a mannose 6-phosphate containing lysosomal protein. The concentration of the mannose 6-phosphate containing lysosomal protein in the milk is usually at least 100 μg/ml.

One useful enzyme expressed by such animals is acid α-glucosidase. Preferred animals for use in the invention include mice, rabbits, goats, sheep, porcines or bovines. The recombinant DNA segment can be cDNA, genomic or a hybrid of the two. In some transgenes, the secretory DNA segment is from the lysosomal protein gene encoded by the recombinant DNA segment.

In another aspect, the invention provides methods for producing a mannose 6-phosphate containing lysosomal protein in the milk of a transgenic mammal. The methods entails recovering milk from the adult form of the transgenic nonhuman mammals described above. Optionally, the mannose 6-phosphate containing protein can be purified from the milk. The purified protein can then be mixed with a pharmaceutical carrier for intravenous, intradermal, intramuscular or oral administration.

In another aspect, the invention provides milk from the transgenic nonhuman mammals described above comprising the mannose 6-phosphate containing lysosomal protein.

DEFINITIONS

The term "substantial identity" or "substantial homology" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity). Preferably, residue positions which are not identical differ by conservative amino acid substitutions.

The term "substantially pure" or "isolated" means an object species has been identified and separated and/or recovered from a component of its natural environment. Usually, the object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent by weight of all macromolecular species present in the composition. Most preferably, the object species is purified to essential homogeneity (contaminant species cannot be detected in the composition by conventional detection methods) wherein the composition consists essentially of derivatives of a single macromolecular species.

A DNA segment is operably linked when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

An exogenous DNA segment is one foreign to the cell, or homologous to a DNA segment of the cell but in an unnatural position in the host cell genome. Exogenous DNA segments are expressed to yield exogenous polypeptides.

In a transgenic mammal, all, or substantially all, of the germline and somatic cells contain a transgene introduced into the mammal or an ancestor of the mammal at an early embryonic stage.

DETAILED DESCRIPTION

The invention provides transgenic nonhuman mammals secreting a mannose 6-phosphate containing lysosomal protein into their milk. Secretion is achieved by incorporation of a transgene encoding a lysosomal protein and regulatory sequences capable of targeting expression of the gene to the mammary gland. The transgene is expressed, and the expression product posttranslationally modified within the mammary gland, and then secreted in milk. The posttranslational modification includes steps of glycosylation and phosphorylation.

A. Lysosomal Genes

The invention provides transgenic nonhuman mammals expressing DNA segments containing any of the more than 30 known genes encoding lysosomal enzymes and other types of lysosomal proteins, including α-glucosidase, α-L-iduronidase, iduronate-sulfate sulfatase, hexosaminidase A and B, ganglioside activator protein, arylsulfatase A and B, iduronate sulfatase, heparan N-sulfatase, galactoceramidase, α-galactosylceramidase A, sphingomyelinase, α-fucosidase, α-mannosidase, aspartylglycosamine amide hydrolase, acid lipase, N-acetyl-α-D-glucosamine-6-sulphate sulfatase, α- and β-galactosidase, β-glucuronidase, β-mannosidase, ceramidase, galactocerebrosidase, α-N-acetylgalactosaminidase, and protective protein and others. Transgenic mammals expressing allelic, cognate and induced variants of any of the known lysosomal protein gene sequences are also included. Such variants usually show substantial sequence identity at the amino acid level with known lysosomal protein genes. Such variants usually hybridize to a known gene under stringent conditions or crossreact with antibodies to a polypeptide encoded by one of the known genes.

DNA clones containing the genomic or cDNA sequences of many of the known genes encoding lysosomal proteins are available. (Scott et al., *Am. J. Hum. Genet.* 47, 802–807 (1990); Wilson et al., *PNAS 87, 8531–8535* (1990); Stein et al., *J. Biol. Chem.* 264, 1252–1259 (1989); Ginns et al., *Biochem. Biophys. Res. Comm.* 123, 574–580 (1984); Hoefsloot et al., *EMBO J.* 7, 1697–1704 (1988); Hoefsloot et al., *Biochem. J.* 272, 473–479 (1990); Meyerowitz & Proia, *PNAS* 81, 5394–5398 (1984); Scriver et al., supra, part 12, pages 2427–2882 and references cited therein)) Other examples of genomic and cDNA sequences are available from GenBank. To the extent that additional cloned sequences of lysosomal genes are required, they may be obtained from genomic or cDNA libraries (preferably human) using known lysosomal protein DNA sequences or antibodies to known lysosomal proteins as probes.

B. Conformation of Lysosomal Proteins

Recombinant lysosomal proteins are preferably processed to have the same or similar structure as naturally occurring lysosomal proteins. Lysosomal proteins are glycoproteins that are synthesized on ribosomes bound to the endoplasmic reticulum (RER). They enter this organelle co-translationally guided by an N-terminal signal peptide (Ng et al., *Current Opinion in Cell Biology* 6, 510–516 (1994)). The N-linked glycosylation process starts in the RER with the en bloc transfer of the high-mannose oligosaccharide precursor $Glc_3MangGlcNAc_2$ from a dolichol carrier. Carbohydrate chain modification starts in the RER and continue in the Golgi apparatus with the removal of the three outermost glucose residues by glycosidases I and II. Phosphorylation is a two-step procedure in which first N-acetylglucosamine-1-phosphate is coupled to select mannose groups by a lysosomal protein specific transferase, and second, the N-acetylglucosamine is cleaved by a diesterase (Goldberg et al., *Lysosomes: Their Role in Protein Breakdown* (Academic Press Inc., London, 1987), pp. 163–191). Cleavage exposes mannose 6-phosphate as a recognition marker and ligand for the mannose 6-phosphate receptor mediating transport of most lysosomal proteins to the lysosomes (Kornfeld, *Biochem. Soc. Trans.* 18, 367–374 (1992)).

In addition to carbohydrate chain modification, most lysosomal proteins undergo proteolytic processing, in which the first event is removal of the signal peptide. The signal peptide of most lysosomal proteins is cleaved after translocation by signal peptidase after which the proteins become soluble. There is suggestive evidence that the signal peptide of acid α-glucosidase is cleaved after the enzyme has left the RER, but before it has entered the lysosome or the secretory pathway (Wisselaar et al., *J. Biol. Chem.* 268, 2223–2231 (1993)). The proteolytic processing of acid α-glucosidase is complex and involves a series of steps in addition to cleavage of the signal peptide taking place at various subcellular locations. Polypeptides are cleaved off at both the N and C terminal ends, whereby the specific catalytic activity is increased. The main species recognized are a 110/100 kDa precursor, a 95 kDa intermediate and 76 kDa and 70 kDa mature forms. (Hasilik et al., *J. Biol. Chem.* 255, 4937–4945 (1980); Oude Elferink et al., *Eur. J. Biochem.* 139, 489–495 (1984); Reuser et al., *J. Biol. Chem.* 260, 8336–8341 (1985); Hoefsloot et al., *EMBO J.* 7, 1697–1704 (1988)). The post translational processing of natural human acid α-glucosidase and of recombinant forms of human acid α-glucosidase as expressed in cultured mammalian cells like COS cells, BHK cells and CHO cells is similar (Hoefsloot et al., (1990) supra; Wisselaar et al., (1993) supra.

Authentic processing to generate lysosomal proteins phosphorylated at the 6' position of the mannose group can be tested by measuring uptake of a substrate by cells bearing a receptor for mannose 6-phosphate. Correctly modified substrates are taken up faster than unmodified substrates, and in a manner whereby uptake of the modified substrate can be competitively inhibited by addition of mannose 6-phosphate.

C. Transgene Design

Transgenes are designed to target expression of a recombinant lysosomal protein to the mammary gland of a transgenic nonhuman mammal harboring the transgene. The basic approach entails operably linking an exogenous DNA segment encoding the protein with a signal sequence, a promoter and an enhancer. The DNA segment can be genomic, minigene (genomic with one or more introns omitted), cDNA, a YAC fragment, a chimera of two different lysosomal protein genes, or a hybrid of any of these. Inclusion of genomic sequences generally leads to higher levels of expression. Very high levels of expression might overload the capacity of the mammary gland to perform posttranslation modifications, and secretion of lysosomal proteins. However, the data presented below indicate that substantial posttranslational modification occurs including the formation of mannose 6-phosphate groups, notwithstanding a high expression level in the mg/ml range. Substantial modification means that at least about 10, 25, 50, 75 or 90% of secreted molecules bear at least one mannose 6-phosphate group. Thus, genomic constructs or hybrid cDNA-genomic constructs are generally preferred.

In genomic constructs, it is not necessary to retain all intronic sequences. For example, some intronic sequences can be removed to obtain a smaller transgene facilitating DNA manipulations and subsequent microinjection. See Archibald et al., WO 90/05188 (incorporated by reference in its entirety for all purposes). Removal of some introns is also useful in some instances to reduce expression levels and thereby ensure that posttranslational modification is substantially complete. It is also possible to delete some or all of noncoding exons. In some transgenes, selected nucleotides in lysosomal protein encoding sequences are mutated to remove proteolytic cleavage sites.

Because the intended use of lysosomal proteins produced by transgenic mammals is usually administration to humans, the species from which the DNA segment encoding a lysosomal protein sequence is obtained is preferably human. Analogously if the intended use were in veterinary therapy (e.g., on a horse, dog or cat), it is preferable that the DNA segment be from the same species.

The promoter and enhancer are from a gene that is exclusively or at least preferentially expressed in the mammary gland (i.e., a mammary-gland specific gene). Preferred genes as a source of promoter and enhancer include β-casein, κ-casein, αS1-casein, αS2-casein, β-lactoglobulin, whey acid protein, and α-lactalbumin. The promoter and enhancer are usually but not always obtained from the same mammary-gland specific gene. This gene is sometimes but not necessarily from the same species of mammal as the mammal into which the transgene is to be expressed. Expression regulation sequences from other species such as those from human genes can also be used. The signal sequence must be capable of directing the secretion of the lysosomal protein from the mammary gland. Suitable signal sequences can be derived from mammalian genes encoding a secreted protein. Surprisingly, the natural signal sequences of lysosomal proteins are suitable, notwithstanding that these proteins are normally not secreted but targeted to an intracellular organelle. In addition to such signal sequences, preferred sources of signal sequences are the signal sequence from the same gene as the promoter and enhancer are obtained. Optionally, additional regulatory sequences are included in the transgene to optimize expression levels. Such sequences include 5' flanking regions, 5' transcribed but untranslated regions, intronic sequences, 3' transcribed but untranslated regions, polyadenylation sites, and 3' flanking regions. Such sequences are usually obtained either from the mammary-gland specific gene from which the promoter and enhancer are obtained or from the lysosomal protein gene being expressed. Inclusion of such sequences produces a genetic milieu simulating that of an authentic mammary gland specific gene and/or that of an authentic lysosomal protein gene. This genetic milieu results in some cases (e.g., bovine αS1-casein) in higher expression of the transcribed gene. Alternatively, 3' flanking regions and untranslated regions are obtained from other heterologous genes such as the β-globin gene or viral genes. The inclusion of 3' and 5' untranslated regions from a lysosomal protein gene, or other heterologous gene can also increase the stability of the transcript.

In some embodiments, about 0.5, 1, 5, 10, 15, 20 or 30 kb of 5' flanking sequence is included from a mammary specific gene in combination with about 1, 5, 10, 15, 20 or 30 kb or 3' flanking sequence from the lysosomal protein gene being expressed. If the protein is expressed from a cDNA sequence, it is advantageous to include an intronic sequence between the promoter and the coding sequence. The intronic sequence is preferably a hybrid sequence formed from a 5' portion from an intervening sequence from the first intron of the mammary gland specific region from which the promoter is obtained and a 3' portion from an intervening sequence of an IgG intervening sequence or lysosomal protein gene. See DeBoer et al., WO 91/08216 (incorporated by reference in its entirety for all purposes).

A preferred transgene for expressing a lysosomal protein comprises a cDNA-genomic hybrid lysosomal protein gene linked 5' to a casein promoter and enhancer. The hybrid gene includes the signal sequence, coding region, and a 3' flanking region from the lysosomal protein gene. Optionally, the cDNA segment includes an intronic sequence between the 5' casein and untranslated region of the gene encoding the lysosomal protein. Of course, corresponding cDNA and genomic segments can also be fused at other locations within the gene provided a contiguous protein can be expressed from the resulting fusion.

Other preferred transgenes have a genomic lysosomal protein segment linked 5' to casein regulatory sequences. The genomic segment is usually contiguous from the 5' untranslated region to the 3' flanking region of the gene. Thus, the genomic segment includes a portion of the lysosomal protein 5' untranslated sequence, the signal sequence, alternating introns and coding exons, a 3' untranslated region, and a 3' flanking region. The genomic segment is linked via the 5' untranslated region to a casein fragment comprising a promoter and enhancer and usually a 5' untranslated region.

DNA sequence information is available for all of the mammary gland specific genes listed above, in at least one, and often several organisms. See, e.g., Richards et al., *J. Biol. Chem.* 256, 526–532 (1981) (α-lactalbumin rat); Campbell et al., *Nucleic Acids Res.* 12, 8685–8697 (1984) (rat WAP); Jones et al., *J. Biol. Chem.* 260, 7042–7050 (1985)) (rat β-casein); Yu-Lee & Rosen, *J. Biol. Chem.* 258, 10794–10804 (1983) (rat γ-casein)); Hall, *Biochem. J.* 242, 735–742 (1987) (α-lactalbumin human); Stewart, *Nucleic Acids Res.* 12, 389 (1984) (bovine αs1 and K casein cDNAs); Gorodetsky et al., *Gene* 66, 87–96 (1988) (bovine β casein); Alexander et al., *Eur. J. Biochem.* 178, 395–401 (1988) (bovine κ casein); Brignon et al., *FEBS Lett.* 188, 48–55 (1977) (bovine αS2 casein); Jamieson et al., *Gene* 61, 85–90 (1987), Ivanov et al., *Biol. Chem. Hoppe-Seyler* 369, 425–429 (1988), Alexander et al., *Nucleic Acids Res.* 17, 6739 (1989) (bovine β lactoglobulin); Vilotte et al., *Biochimie* 69, 609–620 (1987) (bovine α-lactalbumin) (incorporated by reference in their entirety for all purposes). The structure and function of the various milk protein genes are reviewed by Mercier & Vilotte, *J. Dairy Sci.* 76, 3079–3098 (1993) (incorporated by reference in its entirety for all purposes). To the extent that additional sequence data might be required, sequences flanking the regions already obtained could be readily cloned using the existing sequences as probes. Mammary-gland specific regulatory sequences from different organisms are likewise obtained by screening libraries from such organisms using known cognate nucleotide sequences, or antibodies to cognate proteins as probes.

General strategies and exemplary transgenes employing αS1-casein regulatory sequences for targeting the expression of a recombinant protein to the mammary gland are described in more detail in DeBoer et al., WO 91/08216 and WO 93/25567 (incorporated by reference in their entirety for all purposes). Examples of transgenes employing regulatory sequences from other mammary gland specific genes have also been described. See, e.g., Simon et al., *Bio/Technology* 6, 179–183 (1988) and WO88/00239 (1988) (β-lactoglobulin regulatory sequence for expression in sheep); Rosen, EP 279,582 and Lee et al., *Nucleic Acids Res.* 16, 1027–1041 (1988) (β-casein regulatory sequence for expression in mice); Gordon, *Biotechnology* 5, 1183 (1987) (WAP regulatory sequence for expression in mice); WO 88/01648 (1988) and *Eur. J. Biochem.* 186, 43–48 (1989) (α-lactalbumin regulatory sequence for expression in mice) (incorporated by reference in their entirety for all purposes).

The expression of lysosomal proteins in the milk from transgenes can be influenced by co-expression or functional inactivation (i.e., knock-out) of genes involved in post translational modification and targeting of the lysosomal proteins. The data in the Examples indicate that surprisingly mammary glands already express modifying enzymes at sufficient quantities to obtain assembly and secretion of mannose 6-phosphate containing proteins at high levels. However, in some transgenic mammals expressing these proteins at high levels, it is sometimes preferable to supplement endogenous levels of processing enzymes with additional enzyme resulting from transgene expression. Such transgenes are constructed employing similar principles to those discussed above with the processing enzyme coding sequence replacing the lysosomal protein coding sequence in the transgene. It is not generally necessary that posttranslational processing enzymes be secreted. Thus, the secretion signal sequence linked to the lysosomal protein coding sequence is replaced with a signal sequence that targets the processing enzyme to the endoplasmic reticulum without secretion. For example, the signal sequences naturally associated with these enzymes are suitable.

D. Transgenesis

The transgenes described above are introduced into non-human mammals. Most nonhuman mammals, including rodents such as mice and rats, rabbits, ovines such as sheep and goats, porcines such as pigs, and bovines such as cattle and buffalo, are suitable. Bovines offer an advantage of large yields of milk, whereas mice offer advantages of ease of transgenesis and breeding. Rabbits offer a compromise of these advantages. A rabbit can yield 100 ml milk per day with a protein content of about 14% (see Buhler et al., *Bio/Technology* 8, 140 (1990)) (incorporated by reference in its entirety for all purposes), and yet can be manipulated and bred using the same principles and with similar facility as mice. Nonviviparous mammals such as a spiny anteater or duckbill platypus are typically not employed.

In some methods of transgenesis, transgenes are introduced into the pronuclei of fertilized oocytes. For some animals, such as mice and rabbits, fertilization is performed in vivo and fertilized ova are surgically removed. In other animals, particularly bovines, it is preferable to remove ova from live or slaughterhouse animals and fertilize the ova in vitro. See DeBoer et al., WO 91/08216. In vitro fertilization permits a transgene to be introduced into substantially synchronous cells at an optimal phase of the cell cycle for integration (not later than S-phase). Transgenes are usually introduced by microinjection. See U.S. Pat. No. 4,873,292. Fertilized oocytes are then cultured in vitro until a pre-implantation embryo is obtained containing about 16–150 cells. The 16–32 cell stage of an embryo is described as a morula. Pre-implantation embryos containing more than 32 cells are termed blastocysts. These embryos show the development of a blastocoel cavity, typically at the 64 cell stage. Methods for culturing fertilized oocytes to the pre-implantation stage are described by Gordon et al., *Methods Enzymol.* 101, 414 (1984); Hogan et al., *Manipulation of the Mouse Embryo: A Laboratory Manual*, C.S.H.L. N.Y. (1986) (mouse embryo); and Hammer et al., *Nature* 315, 680 (1985) (rabbit and porcine embryos); Gandolfi et al. *J. Reprod. Fert.* 81, 23–28 (1987); Rexroad et al., *J. Anim. Sci.* 66, 947–953 (1988) (ovine embryos) and Eyestone et al. *J. Reprod. Fert.* 85, 715–720 (1989); Camous et al., *J. Reprod. Fert.* 72, 779–785 (1984); and Heyman et al. *Theriogenology* 27, 5968 (1987) (bovine embryos) (incorporated by reference in their entirety for all purposes). Sometimes pre-implantation embryos are stored frozen for a period pending implantation. Pre-implantation embryos are transferred to the oviduct of a pseudopregnant female resulting in the birth of a transgenic or chimeric animal depending upon the stage of development when the transgene is integrated. Chimeric mammals can be bred to form true germline transgenic animals.

Alternatively, transgenes can be introduced into embryonic stem cells (ES). These cells are obtained from preimplantation embryos cultured in vitro. Bradley et al., *Nature* 309, 255–258 (1984) (incorporated by reference in its entirety for all purposes). Transgenes can be introduced into such cells by electroporation or microinjection. Transformed ES cells are combined with blastocysts from a nonhuman animal. The ES cells colonize the embryo and in some embryos form the germline of the resulting chimeric animal. See Jaenisch, *Science*, 240, 1468–1474 (1988) (incorporated by reference in its entirety for all purposes). Alternatively, ES cells can be used as a source of nuclei for transplantation into an enucleated fertilized oocyte giving rise to a transgenic mammal.

For production of transgenic animals containing two or more transgenes, the transgenes can be introduced simultaneously using the same procedure as for a single transgene. Alternatively, the transgenes can be initially introduced into separate animals and then combined into the same genome by breeding the animals. Alternatively, a first transgenic animal is produced containing one of the transgenes. A second transgene is then introduced into fertilized ova or embryonic stem cells from that animal. In some embodiments, transgenes whose length would otherwise exceed about 50 kb, are constructed as overlapping fragments. Such overlapping fragments are introduced into a fertilized oocyte or embryonic stem cell simultaneously and undergo homologous recombination in vivo. See Kay et al., WO 92/03917 (incorporated by reference in its entirety for all purposes).

E. Characteristics of Transgenic Mammals

Transgenic mammals of the invention incorporate at least one transgene in their genome as described above. The transgene targets expression of a DNA segment encoding a lysosomal protein at least predominantly to the mammary gland. Surprisingly, the mammary glands are capable of expressing proteins required for authentic posttranslation processing including steps of oligosaccharide addition and phosphorylation. Processing by enzymes in the mammary gland results in phosphorylation of the 6' position of mannose groups.

Lysosomal proteins can be secreted at high levels of at least 10, 50, 100, 500, 1000, 2000, 5000 or 10,000 $\mu$g/ml. Surprisingly, the transgenic mammals of the invention exhibit substantially normal health. Secondary expression of lysosomal proteins in tissues other than the mammary gland does not occur to an extent sufficient to cause deleterious effects. Moreover, exogenous lysosomal protein produced in the mammary gland is secreted with sufficient efficiency that no significant problem is presented by deposits clogging the secretory apparatus.

The age at which transgenic mammals can begin producing milk, of course, varies with the nature of the animal. For transgenic bovines, the age is about two-and-a-half years naturally or six months with hormonal stimulation, whereas for transgenic mice the age is about 5–6 weeks. Of course, only the female members of a species are useful for producing milk. However, transgenic males are also of value for breeding female descendants. The sperm from transgenic males can be stored frozen for subsequent in vitro fertilization and generation of female offspring.

F. Recovery of Proteins from Milk

Transgenic adult female mammals produce milk containing high concentrations of exogenous lysosomal protein. The protein can be purified from milk, if desired, by virtue of its distinguishing physical and chemical properties, and standard purification procedures such as precipitation, ion exchange, molecular exclusion or affinity chromatography. See generally Scopes, *Protein Purification* (Springer-Verlag, N.Y., 1982)

G. Uses of Recombinant Lysosomal Proteins

The recombinant lysosomal proteins produced according to the invention find use in enzyme replacement therapeutic procedures. A patient having a genetic or other deficiency resulting in an insufficiency of functional lysosomal enzyme can be treated by administering exogenous enzyme to the patient. Patients in need of such treatment can be identified from symptoms (e.g., Hurler's syndrome symptoms include Dwarfism, corneal clouding, hepatosplenomegaly, valvular lesions, coronary artery lesions, skeletal deformities, joint stiffness and progressive mental retardation). Alternatively, or additionally, patients can be diagnosed from biochemical analysis of a tissue sample to reveal excessive accumulation of a characteristic metabolite processed by a particular lysosomal enzyme or by enzyme assay using an artificial or natural substrate to reveal deficiency of a particular lysosomal enzyme activity. For most diseases, diagnosis can be made by measuring the particular enzyme deficiency or by DNA analysis before occurrence of symptoms or excessive accumulation of metabolites (Scriver et al., supra, chapters on lysosomal storage disorders). All of the lysosomal storage diseases are hereditary. Thus, in offspring from families known to have members suffering from lysosomal diseases, it is sometimes advisable to commence prophylactic treatment even before a definitive diagnosis can be made.

In some methods, lysosomal enzymes are administered in purified form together with a pharmaceutical carrier as a pharmaceutical composition. The preferred form depends on the intended mode of administration and therapeutic application. The pharmaceutical carrier can be any compatible, nontoxic substance suitable to deliver the polypeptides to the patient. Sterile water, alcohol, fats, waxes, and inert solids may be used as the carrier. Pharmaceutically-acceptable adjuvants, buffering agents, dispersing agents, and the like, may also be incorporated into the pharmaceutical compositions.

The concentration of the enzyme in the pharmaceutical composition can vary widely, i.e., from less than about 0.1% by weight, usually being at least about 1% by weight to as much as 20% by weight or more.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

A typical composition for intravenous infusion could be made up to contain 100 to 500 ml of sterile 0.9% NaCl or 5% glucose optionally supplemented with a 20% albumin solution and 100 to 500 mg of a enzyme. A typical pharmaceutical compositions for intramuscular injection would be made up to contain, for example, 1 ml of sterile buffered water and 1 to 10 mg of the purified ligand of the present invention. Methods for preparing parenterally administrable compositions are well known in the art and described in more detail in various sources, including, for example, *Remington's Pharmaceutical Science* (15th ed., Mack Publishing, Easton, Pa., 1980) (incorporated by reference in its entirety for all purposes).

The pharmaceutical compositions of the present invention are usually administered intravenously. Intradermal, intramuscular or oral administration is also possible in some circumstances. The compositions can be administered for prophylactic treatment of individuals suffering from, or at risk of, a lysosomal enzyme deficiency disease. For therapeutic applications, the pharmaceutical compositions are administered to a patient suffering from established disease in an amount sufficient to reduce the concentration of accumulated metabolite and/or prevent or arrest further accumulation of metabolite. For individuals at risk of lysosomal enzyme deficiency disease, the pharmaceutical composition are administered prophylactically in an amount sufficient to either prevent or inhibit accumulation of metabolite. An amount adequate to accomplish this is defined as a "therapeutically-" or "prophylactically-effective dose." Such effective dosages will depend on the severity of the condition and on the general state of the patient's health, but will generally range from about 0.1 to 10 mg of purified enzyme per kilogram of body weight.

Lysosomal proteins produced in the milk of transgenic animals have a number of other uses. For example, α-glucosidase, in common with other α-amylases, is an important tool in production of starch, beer and pharmaceuticals. See Vihinen & Mantsala, *Crit. Rev. Biochem. Mol. Biol.* 24, 329–401 (1989) (incorporated by reference in its entirety for all purpose). Lysosomal proteins are also useful for producing laboratory chemicals or food products. For example, acid α-glucosidase degrades 1,4 and 1,6 α-glucosidic bounds and can be used for the degradation of various carbohydrates containing these bonds, such as maltose, isomaltose, starch and glycogen, to yield glucose. Acid α-glucosidase is also useful for administration to patients with an intestinal maltase or isomaltase deficiency. Symptoms otherwise resulting from the presence of undigested maltose are avoided. In such applications, the enzyme can be administered without prior fractionation from milk, as a food product derived from such milk (e.g., ice cream or cheese) or as a pharmaceutical composition. Purified recombinant lysosomal enzymes are also useful for inclusion as controls in diagnostic kits for assay of unknown quantities of such enzymes in tissue samples.

EXAMPLES

Example 1

Construction of Transgenes (a) cDNA construct

Figure 1:
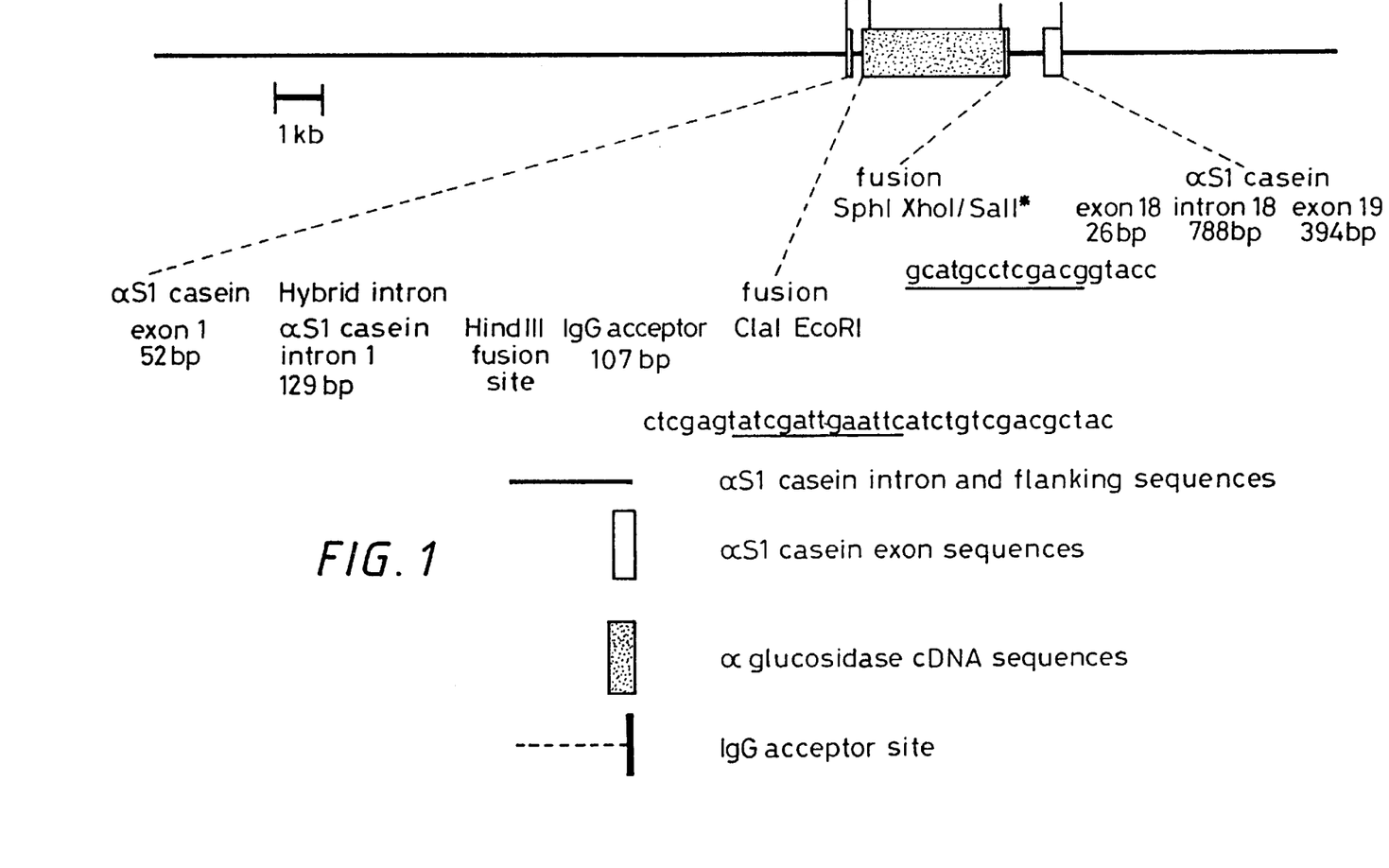
FIG. 1: A transgene containing acid α-glucosidase cDNA. The αs1-casein exons are represented by open boxes; α-glucosidase cDNA is represented by a shaded box. The αs1-casein intron and flanking sequences are represented by a thick line. A thin line represents the IgG acceptor site. The transcription initiation site is marked (⌐), the translation initiation site (ATG), the stopcodon (TAG) and the polyadenylation site (pA).

Construction of an expression vector containing cDNA encoding human acid α-glucosidase started with the plasmid p16,8hlf3 (see DeBoer et al. (1991) & (1993), supra) This plasmid includes bovine αS1-casein regulatory sequences. The lactoferrin cDNA insert of the parent plasmid was exchanged for the human acid α-glucosidase cDNA (Hoefsloot et al. *EMBO J.* 7,1697–1704 (1988)) at the ClaI site and SalI site of the expression cassette as shown in FIG. 1. To obtain the compatible restriction sites at the ends of the α-glucosidase cDNA fragment, plasmid pSHAG2 (id.) containing the complete cDNA encoding human α-glucosidase was digested with EcoRI and SphI and the 3.3 kb cDNA-fragment was subcloned in pKUN7ΔC a pKUN1 derivative (Konings et al., *Gene* 46, 269–276 (1986)), with a destroyed ClaI site within the vector nucleotide sequences and with a newly designed polylinker: HindIII ClaI EcoRI SphI XhoI EcoRI SfiI SfiI/SmaI NotI EcoRI*(*=destroyed site). From the resulting plasmid pαgluCESX, the 3.3-kb cDNA-fragment could be excised by ClaI and XhoI. This fragment was inserted into the expression cassette shown in FIG. 1 at the ClaI site and XhoI-compatible SalI site. As a result, the expression plasmid p16,8αglu consists of the cDNA sequence encoding human acid α-glucosidase flanked by bovine αS1-casein sequences as shown in FIG. 1. The 27.3-kb fragment containing the complete expression cassette can be excised by cleavage with NotI (see FIG. 1).

(b) Genomic Constructs

Figure 2A:
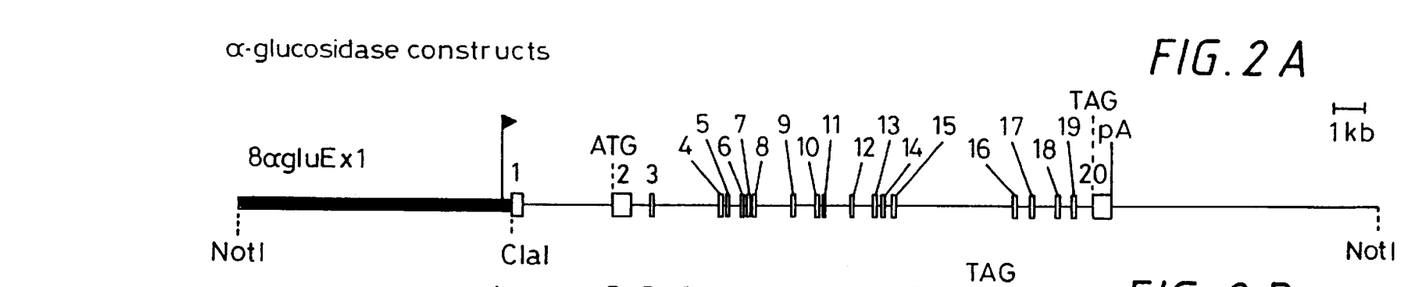
FIG. 2 (panels A, B, C): Three transgenes containing acid α-glucosidase genomic DNA. Dark shaded areas are αs1 casein sequences, open boxes represent acids α-glucosidase exons, and the thin line between the open boxes represents α-glucosidase introns. Other symbols are the same as in FIG. 1.
Figures 2B, 2C:
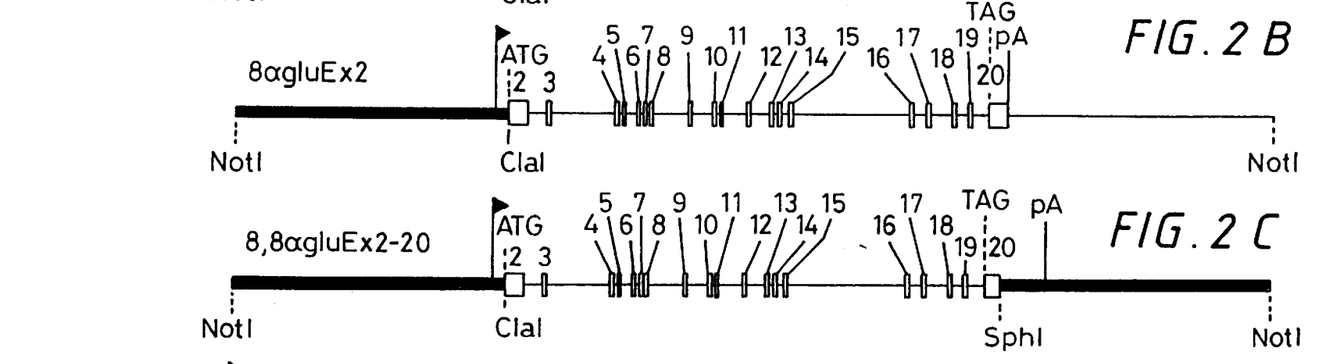

Construct c8αgluex1 contains the human acid α-glucosidase gene (Hoefsloot et al., *Biochem. J.* 272, 493—497 (1990)); starting in exon 1 just downstream of its transcription initiation site (see FIG. 2, panel A). Therefore, the construct encodes almost a complete 5' UTR of the human acid α-glucosidase gene. This fragment was fused to the promoter sequences of the bovine αS1-casein gene. The αS1-casein initiation site is present 22 bp upstream of the αS1-casein/acid α-glucosidase junction. The construct has the human acid α-glucosidase polyadenylation signal and 3' flanking sequences. Construct c8αgluex2 contains the bovine αS1-casein promoter immediately fused to the translation initiation site in exon 2 of the human acid α-glucosidase gene (see FIG. 2, panel B). Thus, the αS1-casein transcription initiation site and the α-glucosidase translation initiation site are 22-bp apart in this construct. Therefore no α-glucosidase 5' UTR is preserved. This construct also contains the human acid α-glucosidase polyadenylation signal and 3' flanking sequences as shown in FIG. 2, panel B.

Construct c8,8αgluex2-20 differs from construct c8αgluex2 only in the 3' region. A SphI site in exon 20 was used to fuse the bovine αS1-casein 3' sequence to the human acid α-glucosidase construct. The polyadenylation signal is located in this 3' αS1-casein sequence (FIG. 2, panel C).

Methods for Construction of Genomic Constructs

Three contiguous BglII fragments containing the human acid α-glucosidase gene were isolated by Hoefsloot et al., supra. These fragments were ligated in the BglII-site of pKUN8ΔC, a pKUN7ΔC derivative with a customized polylinker: HindIII ClaI StuI SstI BglII PvnI NcoI EcoRI SphI XhoI EcoRI* SmaI/SfiI NotI EcoRI* (*=destroyed site). This ligation resulted in two orientations of the fragments generating plasmids p7.3αgluBES, p7.3αgluBSE, p8.5αgluBSE, p8.5αgluBES, p10αagluBSE and p10αgluBES.

Because unique NotI-sites at the ends of the expression cassette are used subsequently for the isolation of the fragments used for microinjection, the intragenic NotI site in intron 17 of human acid α-glucosidase had to be destroyed. Therefore, p10αgluBES was digested with ClaI and XhoI; the fragment containing the 3' α-glucosidase end was isolated. This fragment was inserted in the ClaI and XhoI sites of pKUN10ΔC, resulting in p10αgluΔNV. Previously pKUN10ΔC (i.e., a derivative of pKUN8ΔC) was obtained by digesting pKUN8ΔC with NotI, filling in the sticky ends with Klenow and subsequently, annealing the plasmid by blunt-ended ligation. Finally, p10αgluΔNV was digested with NotI. These sticky ends were also filled with Klenow and the fragment was ligated, resulting in plasmid p10αgluΔNotI.

Construction of c8αgluex1

Since the SstI site in first exon of the α-glucosidase gene was chosen for the fusion to the bovine αS1-casein sequence, p8.5αgluBSE was digested with BglII followed by a partial digestion with SstI. The fragment containing exon 1–3 was isolated and ligated into the BglII and SstI sites of pKUN8ΔC. The resulting plasmid was named: p5'αgluex1 (see FIG. 3, panel A).

The next step (FIG. 3, panel B) was the ligation of the 3' part to p5'αgluex1. First, p10αgluAN was digested with BglII and BamHI. This fragment containing exon 16–20 was isolated. Second, p5'αgluex1 was digested with BglII and to prevent self-ligation, and treated with phosphorylase (BAP) to dephosphorylate the sticky BglII ends. Since BamHI sticky ends are compatible with the BglII sticky ends, these ends ligate to each other. The resulting plasmid, i.e., p5'3'αgluexl, was selected. This plasmid has a unique BglII site available for the final construction step (see FIG. 3, panels B and C).

Figure 3A:
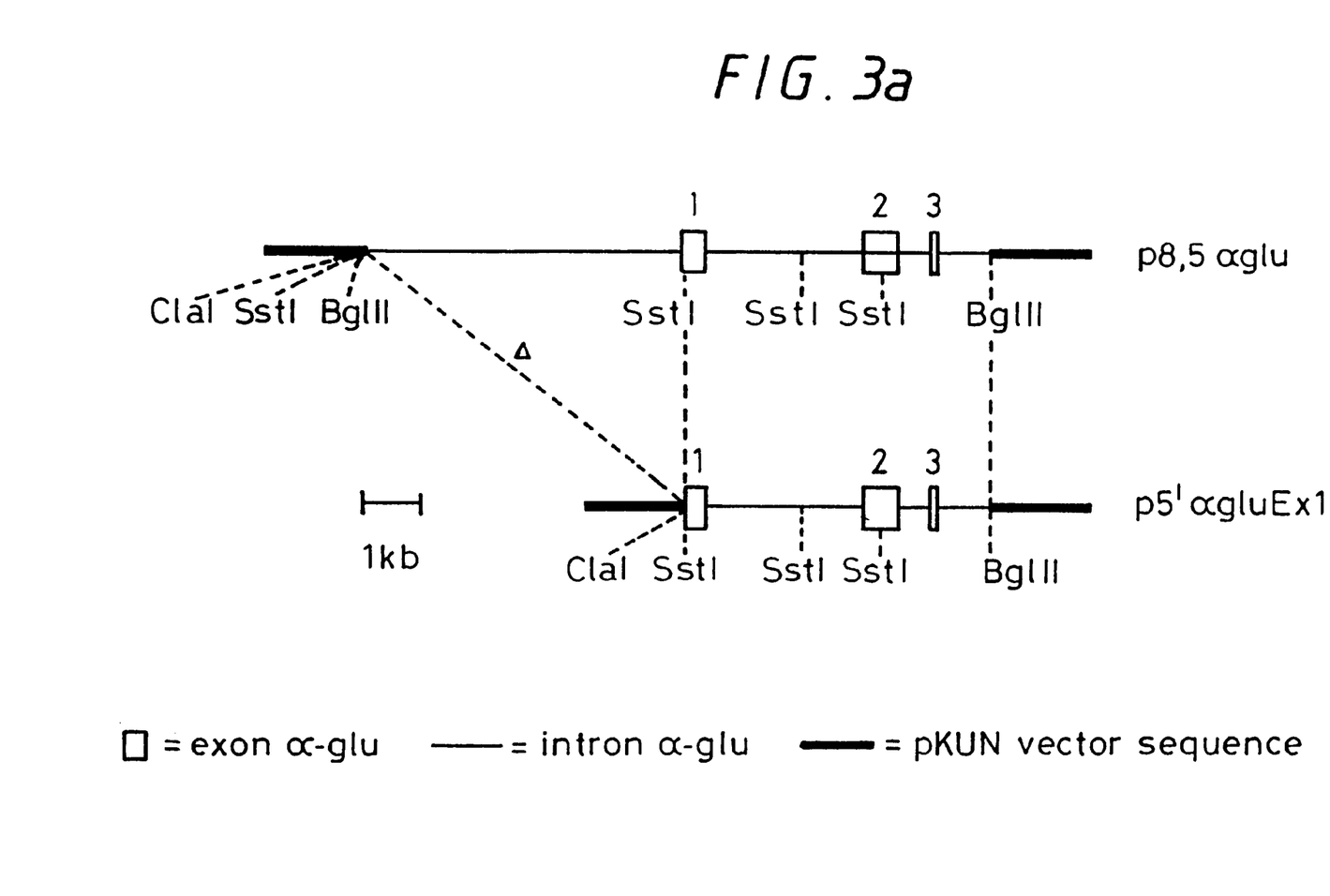
FIG. 3 (panels A, B, C): Construction of genomic transgenes. The α-glucosidase exons are represented by open boxes; the α-glucosidase introns and nontranslated sequences are indicated by thin lines. The pKUN vector sequences are represented by thick lines.
Figure 3B:
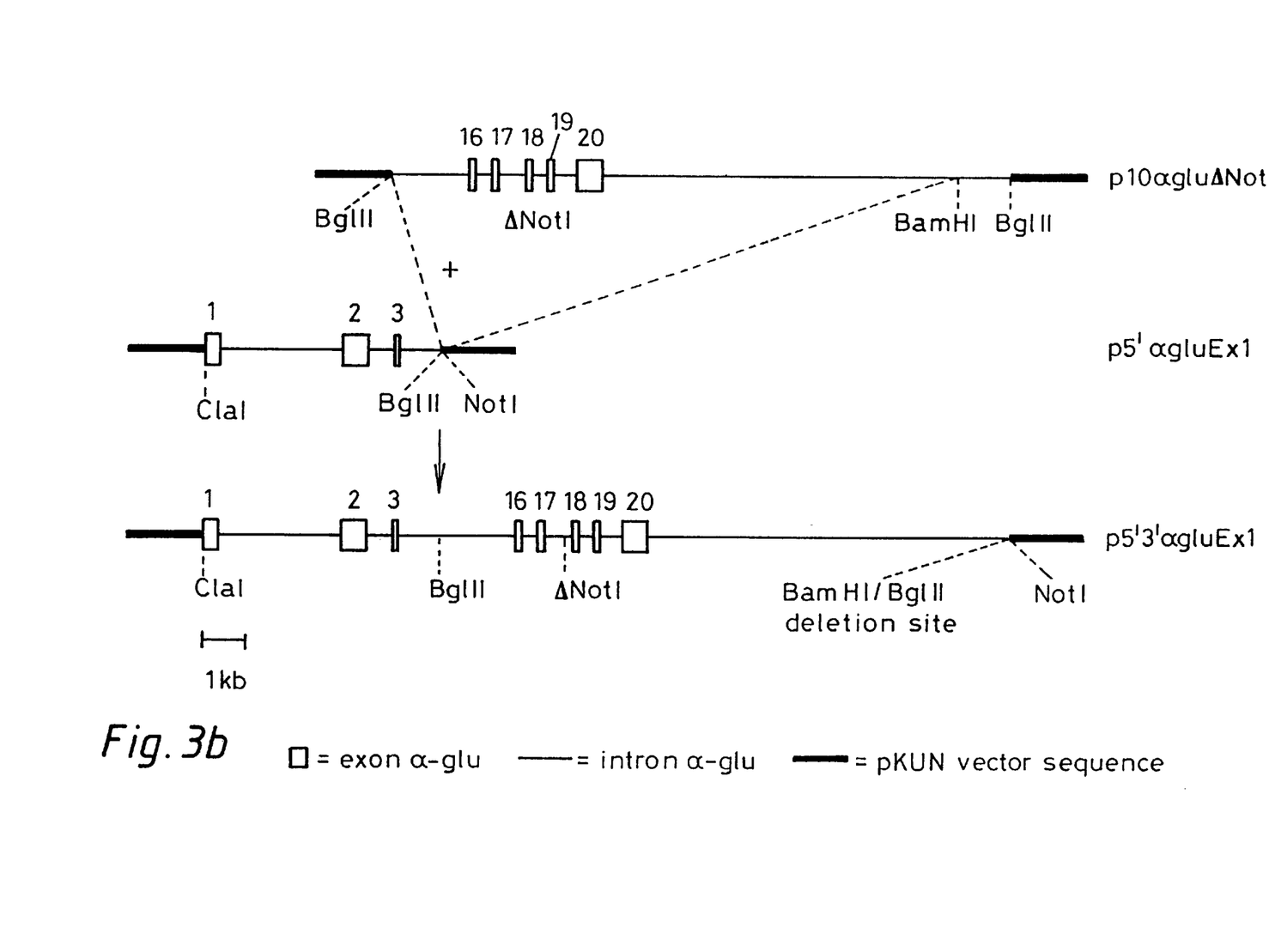
Figure 3C:
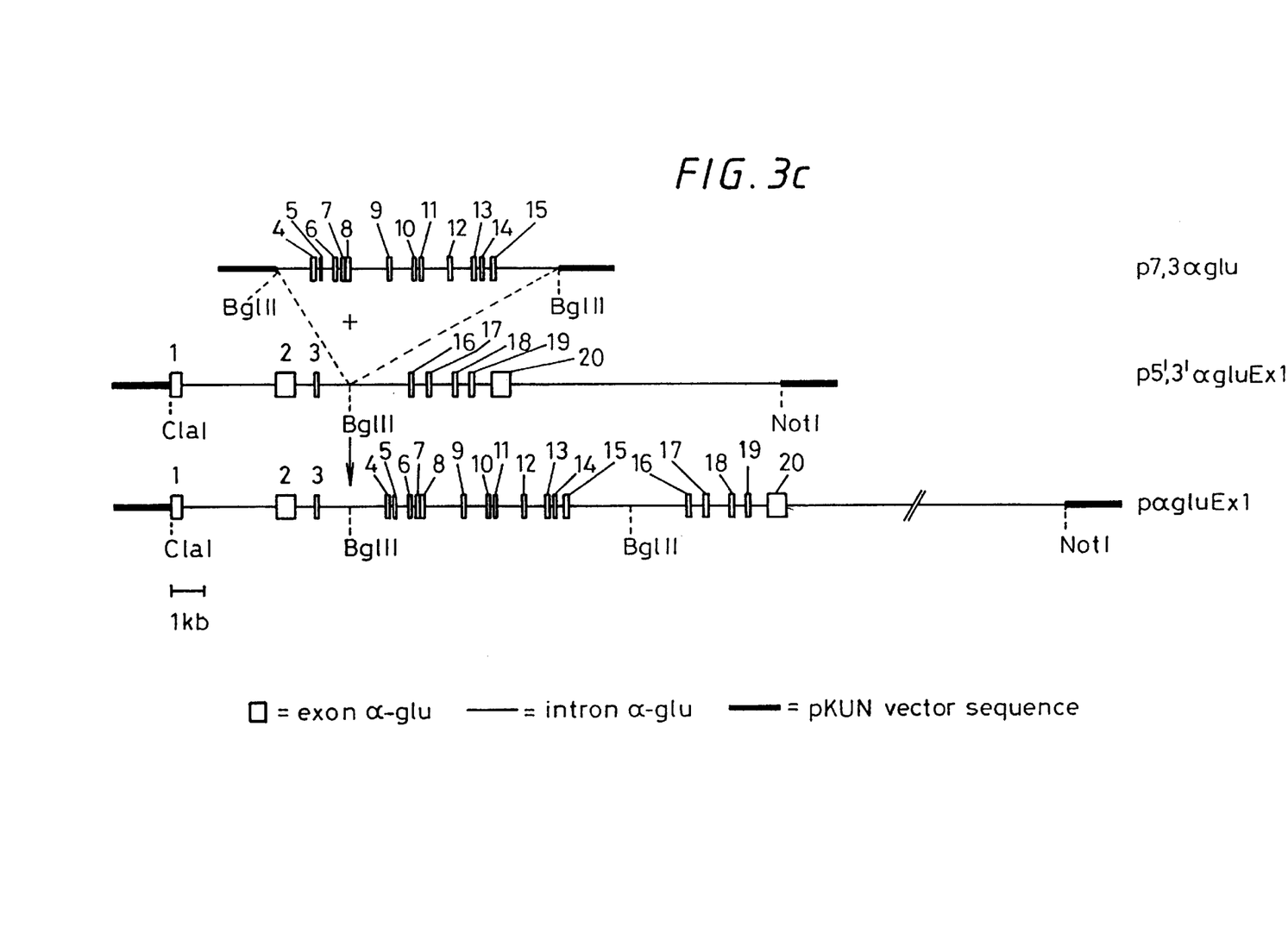

The middle part of the α-glucosidase gene was inserted into the latter construct. For this step, p7.3αgluBSE was digested with BglII, the 8.5-kb fragment was isolated and ligated to the BglII digested and dephosphorylated p5'3'αgluex1 plasmid. The resulting plasmid is pαgluex1 (FIG. 3, panel C).

The bovine αS1-casein promoter sequences were incorporated in the next step via a ligation involving three fragments. The pWE15 cosmid vector was digested with NotI and dephosphorylated. The bovine αs1-casein promoter was isolated as an 8 Rb NotI-ClaI fragment (see de Boer et al., 1991, supra). The human acid α-glucosidase fragment was isolated from pαgluex1 using the same enzymes. These three fragments were ligated and packaged using the Stratagene GigapackII kit in 1046 *E.coli* host cells. The resulting cosmid c8αgluex1 was propagated in *E.coli* strain DH5α. The vector was linearized with NotI before microinjection.

Construction of c8αgluex2 and c8,8αgluex2-20

The construction of the other two expression plasmids (FIG. 2, panels B and C) followed a similar strategy to that of c8αgluex1. The plasmid p5'αgluStuI was derived from p8,5αgluBSE by digestion of the plasmid with StuI, followed by self-ligation of the isolated fragment containing exon 2–3 plus the vector sequences. Plasmid p5'αgluStuI was digested with PglII followed by a partial digestion of the linear fragment with NcoI resulting in several fragments. The 2.4 kb fragment, containing exon 2 and 3, was isolated and ligated into the NcoI and BglII sites of vector pKUN12ΔC, resulting in p5'αgluex2. Note that pKUN12ΔC is a derivative of pKUN8ΔC containing the polylinker: ClaI NcoI BglII HindIII EcoRI SphI XhoI SmaI/SfiI NotI.

The plasmid p10αgluΔNotI was digested with BglII and HindIII. The fragment containing exons 16–20 was isolated and ligated in p5'αgluex2 digested with BglIII and HindIII. The resulting plasmid was p5'3'αgluex2. The middle fragment in p5'3'αgluex2 was inserted as for pαgluex1. For this, p7.3αglu was digested with BglII. The fragment was isolated and ligated to the BglII-digested and dephosphorylated p5'3'αgluex2. The resulting plasmid, pαgluex2, was used in construction of c8αgluex-20 and c8,8αgluex2-20 (FIG. 2, panels B and C).

For the construction of third expression plasmid c8,8α gluex2-20 (FIG. 2, panel C) the 3' flanking region of α-glucosidase was deleted. To achieve this, pαgluex2 was digested with SphI. The fragment containing exon 2–20 was isolated and self-ligated resulting in pαgluex2-20. Subsequently, the fragment containing the 3' flanking region of bovine αs1-casein gene was isolated from p16,8αglu by digestion with SphI and NotI. This fragment was inserted into pαgluex2-20 using the SphI site and the NotI site in the polylinker sequence resulting in pαgluex2-20-3αS1.

The final step in generating c8,8αgluex2-20 was the ligation of three fragments as in the final step in the construction leading to c8αgluex1. Since the ClaI site in pαgluex2-20-3'αS1 and pαgluex2 appeared to be uncleavable due to methylation, the plasmids had to be propagated in the *E. coli* DAM(-) strain ECO343. The pαgluex2-20-3'αS1 isolated from that strain was digested with ClaI and NotI. The fragment containing exons 2–20 plus the 3' αS1-casein flanking region was purified from the vector sequences. This fragment, an 8 kb NotI-ClaI fragment containing the bovine αs1 promoter (see DeBoer (1991) & (1993), supra) and NotI-digested, dephosphorylated pWE15 were ligated and packaged. The resulting cosmid is c8,8αgluex2-20.

Cosmid c8αgluex2 (FIG. 2, panel B) was constructed via a couple of different steps. First, cosmid c8,8αgluex2-20 was digested with SalI and NotI. The 10.5-kb fragment containing the αS1-promoter and the exons 2–6 part of the acid α-glucosidase gene was isolated. Second, plasmid pαgluex2 was digested with SalI and NotI to obtain the fragment containing the 3' part of the acid α-glucosidase gene. Finally, the cosmid vector pWE15 was digested with NotI and dephosphorylated. These three fragments were ligated and packaged. The resulting cosmid is c8αgluex2.

Example 2

Transgenesis

The cNA and genomic constructs were linearized with NotI and injected in the pronucleus of fertilized mouse oocytes which were then implanted in the uterus of pseudopregnant mouse foster mothers. The offspring were analyzed for the insertion of the human α-glucosidase cDNA or genomic DNA gene construct by Southern blotting of DNA isolated from clipped tails. Transgenic mice were selected and bred.

The genomic constructs linearized with NotI were also injected into the pronucleus of fertilized rabbit oocytes, which were implanted in the uterus of pseudopregnant rabbit foster mothers. The offspring were analyzed for the insertion of the alpha-glucosidase DNA by Southern blotting. Transgenic rabbits were selected and bred.

Example 3

Analysis of Acid α-Glucosidase in the Milk of Transgenic Mice

Figure 4A:
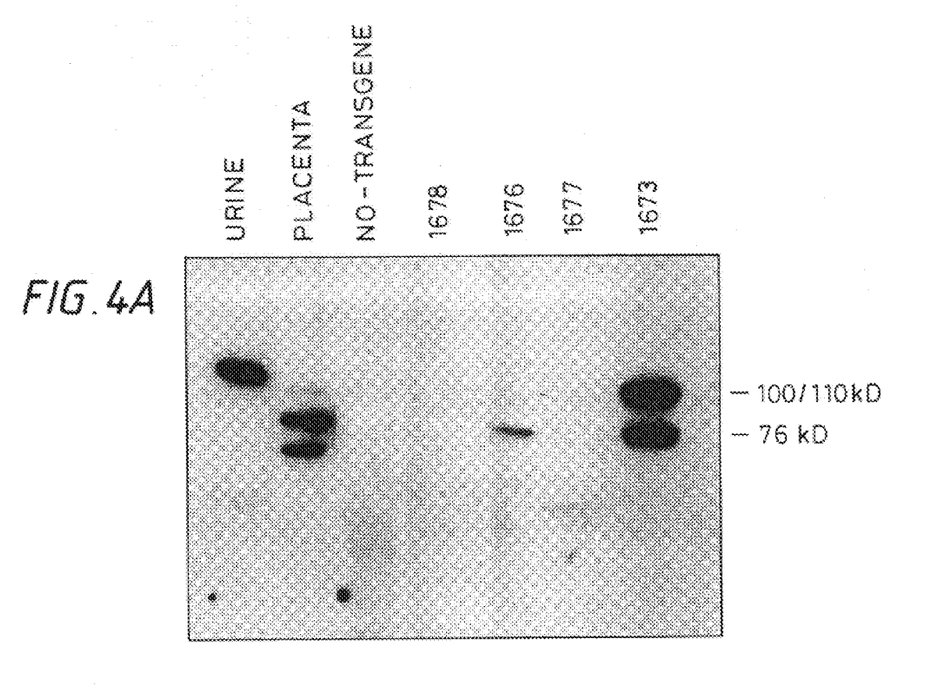
FIG. 4 (panels A and B). Detection of acid α-glucosidase in milk of transgenic mice by Western blotting.
Figure 4B:
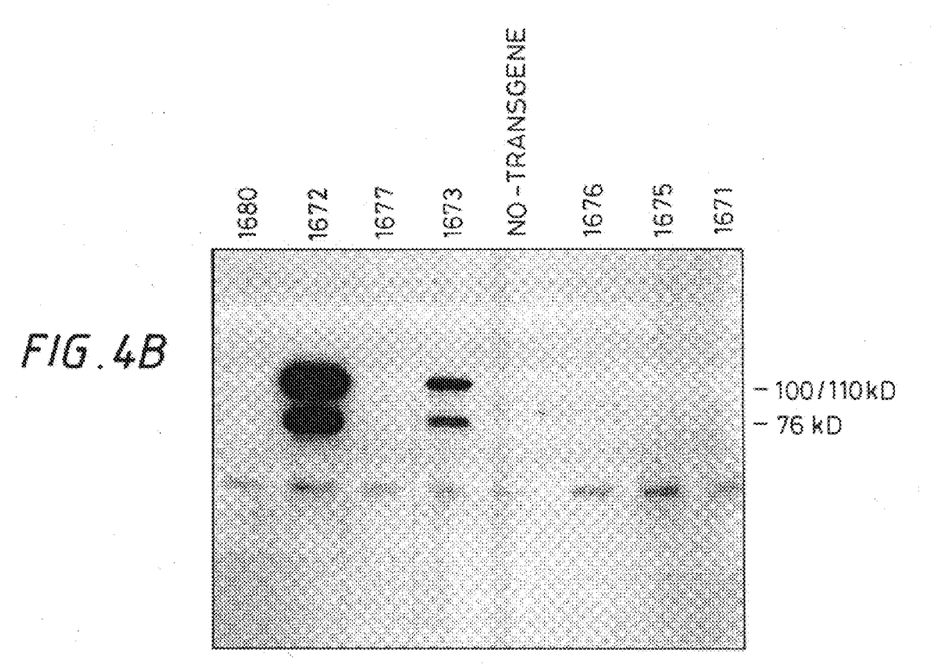

Milk from transgenic mice and nontransgenic controls was analyzed by Western Blotting. The probe was mouse antibody specific for human acid α-glucosidase (i.e, does not bind to the mouse enzyme). Transgenes 1672 and 1673 showed expression of human acid α-glucosidase in milk (FIG. 4). Major and minor bands at 100–110 kD and 76 kD were observed as expected for α-glucosidase. In milk from non-transgenic mice, no bands were observed.

The activity of human acid α-glucosidase was measured with the artificial substrate 4-methylumbelliferyl-α-D-glucopyranoside in the milk of transgenic mouse lines (See Galiaard, *Genetic Metabolic Disease, Early Diagnosis and Prenatal Analysis*, Elsevier/North Holland, Amsterdam, pp. 809–827 (1980)). Mice containing the cDNA construct (FIG. 1) varied from 0.2 to 2 μmol/ml per hr. The mouse lines containing the genomic construct (FIG. 2, panel A) expressed at levels from 10 to 610 μmol/ml per hr. These figures are equivalent to a production of 1.3 to 11.3 mg/l (cDNA construct) and 0.05 to 3.3 g/l (genomic construct) based on an estimated specific activity of the recombinant enzyme of 180 μmol/mg (Van der Ploeg et al., *J. Neurol.* 235:392–396 (1988)).

The recombinant acid α-glucosidase was isolated from the milk of transgenic mice, by sequential chromatography of milk on ConA-Sepharose™ and Sephadex™ G200. 7 ml milk was diluted to 10 ml with 3 ml Con A buffer consisting of 10 mM sodium phosphate, pH 6.6 and 100 mM NaCl. A 1:1 suspension of Con A sepharose in Con A buffer was then added and the milk was left overnight at 4° C. with gentle shaking. The Con A sepharose beads were then collected by centrifugation and washed 5 times with Con A buffer, 3 times with Con A buffer containing 1 M NaCl instead of 100 mM, once with Con A buffer containing 0.5 M NaCl instead of 100 mM and then eluted batchwise with Con A buffer containing 0.5 M NaCl and 0.1 M methyl-α-D-mannopyranoside. The acid α-glucosidase activity in the eluted samples was measured using the artificial 4-methylumbelliferyl-α-D-glycopyranoside substrate (see above). Fractions containing acid α-glucosidase activity were pooled, concentrated and dialyzed against Sephadex buffer consisting of 20 mM Na acetate, pH 4.5 and 25 mM NaCl, and applied to a Sephadex™ 200 column. This column was run with the same buffer, and fractions were assayed for acid α-glucosidase activity and protein content. Fractions rich in acid α-glucosidase activity and practically free of other proteins were pooled and concentrated. The method as described is essentially the same as the one published by Reuser et al., *Exp. Cell Res.* 155:178–179 (1984). Several modifications of the method are possible regarding the exact composition and pH of the buffer systems and the choice of purification steps in number and in column material.

Acid α-glucosidase purified from the milk was then tested for phosphorylation by administrating the enzyme to cultured fibroblasts from patients with GSD II (deficient in endogenous acid α-glucosidase). In this test mannose 6-phosphate containing proteins are bound by mannose 6-phosphate receptors on the cell surface of fibroblasts and are subsequently internalized. The binding is inhibited by free mannose 6-phosphate (Reuser et al., *Exp. Cell Res.* 155:178–189 (1984)). In a typical test for the phosphorylation of acid α-glucosidase isolated from milk of transgenic mice, the acid α-glucosidase was added to $10^4$–$10^6$ fibroblasts in 500 μl culture medium (Ham F10, supplied with 10% fetal calf serum and 3 mM Pipes) in an amount sufficient to metabolize 1 μmole 4-methyl-umbelliferyl-α-D-glucopyranoside per hour for a time period of 20 hours. The experiment was performed with or without 5 mM mannose 6-phosphate as a competitor, essentially as described by Reuser et al., supra (1984). Under these conditions acid α-glucosidase of the patient fibroblasts was restored to the level measured in fibroblasts from healthy individuals. The restoration of the endogenous acid α-glucosidase activity by acid α-glucosidase isolated from mouse milk was as efficient as restoration by acid α-glucosidase purified from bovine testis, human urine and medium of transfected CHO cells. Restoration by α-glucosidase form milk was inhibited by 5 mM mannose 6-phosphate as observed for α-glucosidase from other sources. (Reuser et al., supra; Van der Ploeg et al., (1988), supra; Van der Ploeg et al., *Ped. Res.* 24:90–94 (1988).

As a further demonstration of the authenticity of α-glucosidase produced in the milk, the N-terminal amino acid sequence of the recombinant α-glucosidase produced in the milk of mice was shown to be the same as that of α-glucosidase precursor from human urine as published by Hoefsloot et al., *EMBO J.* 7:1697–1704 (1988) which starts with AHPGRP.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A transgenic nonhuman mammal having a transgene comprising:
    a promoter and enhancer from the same mammary gland specific gene;
    a secretory DNA segment encoding a signal peptide functional in mammary secretory cells of the transgenic nonhuman mammal, and
    a recombinant DNA segment encoding acid α-glucosidase operably linked to the secretory DNA segment to form a secretory-recombinant DNA segment, the secretory-recombinant DNA segment being operably linked to the promoter and enhancer, and wherein the secretory DNA segment is an acid a glucosidase secretory DNA segment or is from the same mammary-gland specific gene as the promoter and enhancer;
    wherein the transgene, in an adult form of the nonhuman mammal or a female descendant of the nonhuman mammal, expresses the secretory-recombinant DNA segment in the mammary secretory cells to produce acid α-glucosidase that is processed and secreted by the mammary secretory cells into milk in a recoverable amount with α-glucosidase catalytic activity.

2. The transgenic nonhuman mammal of claim 1, wherein the concentration of the acid α-glucosidase in the milk is at least 100 μg/ml.

3. The nonhuman transgenic mammal of claim 1, wherein the secretory DNA segment is an acid α-glucosidase secretory DNA segment.

4. The transgenic nonhuman mammal of claim 1, wherein the human acid α-glucosidase is secreted into milk in a form that can be taken up by muscle cells.

5. The nonhuman transgenic mammal of claim 1, wherein the acid α-glucosidase is human.

6. The nonhuman transgenic mammal of claim 5, that is a mouse or rabbit.

7. The nonhuman transgenic mammal of claim 6, wherein the recombinant DNA segment is cDNA.

8. The nonhuman transgenic mammal of claim 6, wherein the recombinant DNA segment is genomic.

9. The nonhuman transgenic mammal of claim 6, wherein the recombinant DNA segment is a cDNA-genomic-DNA hybrid.

10. A method for producing acid α-glucosidase, the method comprising:
    recovering milk from the adult form of the transgenic nonhuman mammal of claim 1 or its female descendant, wherein said milk contains a recoverable amount of acid α-glucosidase with catalytic activity.

11. The method of claim 10, further comprising incorporating the milk into a food product.

12. The method of claim 10, further comprising purifying the acid α-glucosidase from the milk.

13. The method of claim 12, wherein the acid α-glucosidase is purified to at least 95% pure from other components of the milk.

14. The method of claim 13, further comprising mixing the acid α-glucosidase with a pharmaceutical carrier for intravenous, intradermal, intramuscular or oral administration.

15. Milk from the transgenic nonhuman mammal of claim 1, the milk comprising human acid α-glucosidase in a recoverable amount.

16. The milk of claim 15, wherein the concentration of the human acid α-glucosidase is at least 100 μg/ml.

17. A composition comprising human acid α-glucosidase with catalytic activity and capacity to be taken up by muscle cells in a patient and milk of the nonhuman transgenic mammal of claim 1.

18. A pharmaceutical composition for parenteral administration to a human patient comprising human acid α-glucosidase with catalytic activity and in a therapeutically effective dosage to treat a patient suffering from Pompe's disease; and a pharmaceutical carrier, the composition being free of other human proteins present in its natural environment.

19. The pharmaceutical composition of claim 18, wherein the pharmaceutical carrier is for intravenous administration.

20. The pharmaceutical composition of claim 18, wherein the human acid α-glucosidase is purified to homogeneity.

* * * * *

UNITED STATES PATENT AND TRADEMARK OFFICE
CERTIFICATE OF CORRECTION

PATENT NO. : 6,118,045
DATED : September 12, 2000
INVENTOR(S) : Arnold J. J. Reuser et al.

It is certified that error appears in the above-identified patent and that said Letters Patent is hereby corrected as shown below:

Column 1,
Lines 6-7, please delete "The present application is of a continuation-in-part of U.S. Ser. No. 60/001,796, filed August 2, 1995" and replace with -- The present application is a nonprovisional and claims the benefit under 35 USC 119(e) of U.S. Serial. No. 60/001,796, filed August 2, 1995. --.

Signed and Sealed this

Twenty-fifth Day of January, 2005

JON W. DUDAS
*Director of the United States Patent and Trademark Office*